United States Patent [19]

Hayes

[11] 4,051,071

[45] Sept. 27, 1977

[54] DEHYDROGENATION METHOD AND SULFIDED NONACIDIC MULTIMETALLIC CATALYTIC COMPOSITE FOR USE THEREIN

[75] Inventor: John C. Hayes, Palatine, Ill.

[73] Assignee: UOP Inc., Des Plaines, Ill.

[21] Appl. No.: 650,574

[22] Filed: Jan. 19, 1976

Related U.S. Application Data

[63] Continuation-in-part of Ser. No. 518,700, Oct. 29, 1974, Pat. No. 3,939,060, which is a continuation-in-part of Ser. No. 288,864, Sept. 13, 1972, Pat. No. 3,846,282.

[51] Int. Cl.$^2$ ............................................. B01J 27/04
[52] U.S. Cl. .............................. 252/439; 260/668 D; 260/669 R; 260/683.3
[58] Field of Search .................... 252/439, 441, 466 B, 252/473, 474

[56] References Cited

U.S. PATENT DOCUMENTS

| | | | |
|---|---|---|---|
| 2,972,644 | 2/1961 | Holmes et al. | 252/474 X |
| 3,271,325 | 9/1966 | Davies et al. | 252/466 B |
| 3,315,007 | 4/1967 | Abell et al. | 252/466 PT X |
| 3,562,346 | 2/1971 | Smirnov et al. | 252/472 X |
| 3,696,167 | 10/1972 | Juguin et al. | 252/466 PT X |

Primary Examiner—Patrick P. Garvin
Attorney, Agent, or Firm—James R. Hoaston, Jr.; Thomas K. McBride; William H. Page, II

[57] ABSTRACT

Dehydrogenatable hydrocarbons are dehydrogenated by contacting them at dehydrogenation conditions, with a sulfided catalytic composite comprising a combination of catalytically effective amounts of a platinum or palladium component, an iridium component, and a nickel component with a porous carrier material. A specific example of the sulfided nonacidic catalytic composite disclosed herein is a combination of a platinum or palladium component, an iridium component, a nickel component, an alkali or alkaline earth component and a sulfur component with a porous carrier material; wherein the metallic components are uniformly dispersed throughout the porous carrier material; wherein substantially all of the platinum or palladium, iridium and nickel components are present therein in the elemental metallic state or in a sulfided state or in a mixture thereof; wherein substantially all of the alkali or alkaline earth component is present therein in an oxidation state above the elemental metal; wherein the composite contains, on an elemental basis, about 0.01 to about 2 wt. % platinum or palladium, about 0.01 to about 2 wt. % iridium, about 0.1 to about 5 wt. % alkali metal or alkaline earth metal, about 0.01 to about 5 wt. % nickel and about 0.01 to about 1 wt. % sulfur; and wherein the composite is sulfided prior to use in the dehydrogenation method and after the metallic components thereof have been reduced to the elemental metallic state.

14 Claims, No Drawings

DEHYDROGENATION METHOD AND SULFIDED NONACIDIC MULTIMETALLIC CATALYTIC COMPOSITE FOR USE THEREIN

CROSS-REFERENCE TO RELATED APPLICATIONS

This application is a continuation-in-part of my prior, copending application Ser. No. 518,700 filed Oct. 29, 1974; now U.S. Pat. No. 3,939,060, issued on Feb. 17, 1976 which in turn is a continuation-in-part of my prior application Ser. No. 288,864 filed Sept. 13, 1972, and now U.S. Pat. No. 3,864,282. All of the teachings of these prior applications are specifically incorporated herein by reference.

The subject of the present invention is, broadly, an improved method for dehydrogenating a dehydrogenatable hydrocarbon to produce a hydrocarbon product containing the same number of carbon atoms but fewer hydrogen atoms. In another aspect, the present invention involves a method of dehydrogenating normal paraffin hydrocarbons containing 4 to 30 carbon atoms per molecule to the corresponding normal mono-olefin with minimum production of side products. In yet another aspect, the present invention relates to a novel sulfided nonacidic multimetallic catalytic composite comprising a combination of catalytically effective amounts of a platinum or palladium component, an iridium component, a nickel component, a sulfur component and an alkali or alkaline earth component with a porous carrier material. This composite has highly beneficial characteristics of activity, selectivity, and stability when it is employed in the dehydrogenation of dehydrogenatable hydrocarbons such as aliphatic hydrocarbons, naphthene hydrocarbons, and alkylaromatic hydrocarbons.

The conception of the present invention followed from my search for a novel catalytic composite possessing a hydrogenation-dehydrogenation function, a controllable cracking function, and superior conversion, selectivity, and stability characteristics when employed in hydrocarbon conversion processes that have traditionally utilized dual-function catalytic composites. In my prior applications, I disclosed a significant finding with respect to a sulfided multimetallic catalytic composite meeting these requirements. More specifically, I determined that a combination of specified amounts of iridium, nickel and sulfur can be utilized, under certain conditions, to beneficially interact with the platinum or palladium component of a dual-function catalyst with a resulting marked improvement in the performance of such a catalyst. Now I have ascertained that a sulfided catalytic composite, comprising a combination of catalytically effective amounts of a platinum or palladium component, an iridium component, a nickel component and a sulfur component with a porous carrier material can have superior activity, selectivity, and stability characteristics when it is employed in a dehydrogenation process if the metallic components are uniformly dispersed in the porous carrier material in the amounts specified hereinafter, if the oxidation state of the metallic ingredients are carefully controlled so that substantially all of the platinum or palladium, iridium and nickel components are present in the elemental metallic state or in a sulfided state or in a mixture thereof, and if the composite is sulfided in the manner indicated hereinbefore use in the dehydrogenation of hydrocarbons and after substantially all of the metallic components are reduced to the corresponding elemental metallic state. Moreover, I have discerned that a particularly preferred sulfided multimetallic catalytic composite of this type contains not only a platinum or palladium component, an iridium component, and a nickel component, but also an alkali or alkaline earth component in an amount sufficient to ensure that the resulting catalyst is nonacidic.

The dehydrogenation of dehydrogenatable hydrocarbons is an important commercial process because of the great and expanding demand for dehydrogenated hydrocarbons for use in the manufacture of various chemical products such as detergents, plastics, synthetic rubbers, pharmaceutical products, high octane gasolines, perfumes, drying oils, ion-exchange resins, and various other products well known to those skilled in the art. One example of this demand is in the manufacture of high octane gasoline by using $C_3$ and $C_4$ mono-olefins to alkylate iso-butane. Another example of this demand is in the area of dehydrogenation of normal paraffin hydrocarbons to produce normal mono-olefins having 4 to 30 carbon atoms per molecule. These normal mono-olefins can, in turn, be utilized in the synthesis of a vast number of other chemical products. For example, derivatives of normal mono-olefins have become of substantial importance to the detergent industry where they are utilized to alkylate an aromatic, such as benzene, with subsequent transformation of the product arylalkane into a wide variety of biodegradable detergents such as the alkylaryl sulfonate types of detergents which are most widely used today for household, industrial, and commercial purposes. Still another large class of detergents produced from these normal mono-olefins are the oxy-alkylated phenol derivatives in which the alkyl phenol base is prepared by the alkylation of phenol with these normal mono-olefins. Still another type of detergents produced from these normal mono-olefins are the biodegradable alkylsulfonates formed by the direct sulfation of the normal mono-olefins. Likewise, the olefin can be subjected to direct sulfonation with sodium bisulfite to make biodegradable alkylsulfonates. As a further example, these mono-olefins can be hydrated to produce alcohols which then, in turn, can be used to produce plasticizers and/or synthetic lube oils.

Regarding the use of products made by the dehydrogenation of alkylaromatic hydrocarbons, they find wide application in the petroleum, petrochemical, pharmaceutical, detergent, plastic, and the like industries. For example, ethylbenzene is dehydrogenated to produce styrene which is utilized in the manufacture of polystyrene plastics, styrene-butadiene rubber, and the like products. Isopropylbenzene is dehydrogenated to form alpha-methylstyrene which, in turn, is extensively used in polymer formation and in the manufacture of drying oils, ion exchange resins, and the like materials.

Responsive to this demand for these dehydrogenation products, the art has developed a number of alternative methods to produce them in commercial quantities. One method that is widely utilized involves the selective dehydrogenation of a dehydrogenatable hydrocarbon by contacting the hydrocarbon with a suitable catalyst at dehydrogenation conditions. As is the case with most catalytic procedures, the principal measure of effectiveness for this dehydrogenation method involves the ability to perform its intended function with minimum interference of side reactions for extended periods of time. The analytical term as used in the art to broadly measure how well a particular catalyst performs its intended functions in a particular hydrocarbon conversion reaction are activity, selectivity, and stability, and for purposes of discussion here, these terms are generally defined for a given reactant as follows: (1) activity is a measure of the catalyst's ability to convert the hydrocarbon reactant into products at a specified severity level where severity level means the specific reaction conditions used — that is, the temperature, pressure, contact time, and presence of diluents such as $H_2$; (2) selectivity usually refers to the amount of desired product or products obtained relative to the amount of the reactant charged or converted; (3) stability refers to the rate of chance with time of the activity and selectivity parameters — obviously the smaller rate implying the more stable catalyst. More specifically, in a dehydrogenation process, activity commonly refers to the amount of conversion that takes place for a given dehydrogenation hydrocarbon at a specified severity level and is typically measured on the basis of disappearance of the dehydrogenatable hydrocarbon; selectivity is typically measured by the amount, calculated on a mole percent of converted dehydrogenatable hydrocarbon basis, of the desired dehydrogenated hydrocarbon obtained at the particular activity or severity level; and stability is typically equated to the rate of change with time of activity as measured by disappearance of the dehydrogenatable hydrocarbon and of selectivity at measured by the amount of desired dehydrogenated hydrocarbon produced. Accordingly, the major problem facing workers in the hydrocarbon dehydrogenation art is the development of a more active and selective catalytic composite that has good stability characteristics.

I have now found a sulfided multimetallic catalytic composite which possesses improved activity, selectivity, and stability when it is employed in a process for the dehydrogenation of dehydrogenatable hydrocarbons. In particular, I have determined that the use of a sulfided multimetallic catalyst, comprising a combination of catalytically effective amounts of a platinum or palladium component, an iridium component, a nickel component and a sulfur component with a porous refractory carrier material, can enable the performance of a dehydrogenation process to be substantially improved if the metallic components are uniformly dispersed throughout the carrier material in the amounts specified hereinafter, if their oxidation states are carefully controlled to be in the states hereinafter specified and if the catalyst is properly sulfided before use in the instant dehydrogentation dehydrogenation Moreover, particularly good results are obtained when this composite is combined with an amount of an alkali or alkaline earth component in an amount sufficient to ensure that the resulting catalyst is nonacidic and utilized to produce dehydrogenated hydrocarbons containing the same carbon structure as the reactant hydrocarbon but fewer hydrogen atoms. This sulfided nonacidic composite is particularly useful in the dehydrogenation of long chain normal paraffins to produce the corresponding normal mono-olefin with minimization of side reactions such as skeletal isomerization, aromatization, cracking and polyolefin formation.

It is, accordingly, one object of the present invention to provide a novel method for the dehydrogenation of dehydrogenatable hydrocarbons utilizing a sulfided multimetallic catalytic composite comprising a platinum or palladium component, an iridium component, a nickel component and a sulfur component combined with a porous carrier material. A second object is to provide a novel nonacidic catalytic composite having superior performance characteristics when utilized in a dehydrogenation process. Another object is to provide an improved method for the dehydrogenation of normal paraffin hydrocarbons to produce normal mono-olefins which method minimizes undesirable side reactions such as cracking, skeletal isomerization, polyolefin formation and aromatization.

In brief summary, one embodiment of the present invention involves a method for dehydrogenating a dehydrogenatable hydrocarbon which comprises contacting the hydrocarbon at dehydrogentation conditions with a sulfided multimetallic catalytic composite comprising a porous carrier material containing a uniform dispersion of catalytically effective amounts of a platinum or palladium component, an iridium component, a nickel component, and a sulfur component. Moreover, substantially all of the platinum or palladium, iridium and nickel components are present in the composite in a sulfided state or in the elemental metallic state or in a mixture of these states. Further these components are present in this composite in amounts, calculated on an elemental basis, sufficient to result in the composite containing about 0.01 to about 2 wt. % platinum or palladium, about 0.01 to about 2 wt. % iridium, about 0.01 to about 5 wt. % nickel and about 0.01 to about 1 wt. % sulfur. The sulfiding of the composite is performed prior to contact with the dehydrogenatable hydrocarbon and after substantially all of the metallic components have been reduced to the elemental metallic state by treatment with a sulfiding gas at sulfiding conditions effective to incorporate about 0.01 to about 1 wt. % sulfur.

A second embodiment relates to the dehydrogenation method described in the first embodiment wherein the dehydrogenatable hydrocarbon is an aliphatic compound containing 2 to 30 carbon atoms per molecule.

A third embodiment comprehends a sulfided nonacidic catalytic composite comprising a porous carrier material having uniformly dispersed therein catalytically effective amounts of a platinum or palladium component, an iridium component, a nickel component, an alkali or alkaline earth component and a sulfur component. These components are preferably present in amounts sufficient to result in the catalytic composite containing, on an elemental basis, about 0.01 to about 2 wt. % platinum or palladium, about 0.1 to about 5 wt. % of the alkali metal or alkaline erth metal, about 0.01 to about 2 wt. % iridium, about 0.01 to about 5 wt. % nickel and about 0.01 to about 1 wt. % sulfur. In addition, substantially all of the platinum or palladium, iridium, and nickel components are present in the sulfided state or in the elemental metallic state or in a mixture of these, and substantially all of the alkali or alkaline earth component is present in an oxidation state above that of the elemental metal. The sulfiding of the composite is performed prior to contact with the dehydrogenatable hydrocarbon and after substantially all of the metallic components have been reduced to the elemental metallic state by treatment with a sulfiding gas at sulfiding conditions effective to incorporate about 0.01 to about 1 wt. % sulfide.

Another embodiment pertains to a method for dehydrogenating a dehydrogenatable hydrocarbon which comprises contacting the hydrocarbon with the catalytic composite described in the third embodiment at dehydrogenation conditions.

Other objects and embodiments of the present invention involve specific details regarding essential and preferred catalytic ingredients, preferred amounts of ingredients, suitable methods of multimetallic composite preparation, suitable dehydrogenatable hydrocarbons, operating conditions for use in the dehydrogenation process, and the like particulars. These are hereinafter give in the following detailed discussion of each of these facets of the present invention. It is to be noted that the term "nonacidic" means that the catalyst produces less than 10% conversion of 1-butene to isobutylene when tested at dehydrogenation conditions and, preferably, less than 1%.

Regarding the dehydrogenatable hydrocarbon that is subjected to the method of the present invention, it can, in general, be an organic compound having 2 to 30 carbon atoms per molecule and containing at least one pair of adjacent carbon atoms having hydrogen attached thereto. That is, it is intended to include within the scope of the present invention, the dehydrogenation of any organic compound capable of being dehydrogenated to produce products containing the same number of carbon atoms but fewer hydrogen atoms, and capable of being vaporized at the dehydrogenation temperatures used herein. More particularly, suitable dehydrogenatable hydrocarbons are: aliphatic compounds containing 2 to 30 carbon atoms per molecule, alkylaromatic hydrocarbons where the alkyl group contains 2 to 6 carbon atoms, and naphthenes or alkyl-substituted naphthenes. Specific examples of suitable dehydrogenatable hydrocarbons are: (1) alkanes such as ethane, propane, n-butane, isobutane, n-pentane, isopentane, n-hexane, 2-methylhexene, 2-methylpentane, 2,2-dimethylbutane, n-heptane, 2-ethylhexane, 2,2,3-trimethylbutane, and the like compounds; (2) naphthenes such as cyclopentane, cyclohexane, methylcyclopentane, ethylcyclopentane, n-propylcyclopentane, 1,3-dimethylcyclohexane, and the like compounds; and (3) alkylaromatics such as ethylbenzene, n-butylbenzene, 1,3,5-triethylbenzene, isopropylbenzene, isobutylbenzene, ethylnaphthalene, and the like compounds.

In a preferred embodiment, the dehydrogenatable hydrocarbon is a normal paraffin hydrocarbon having about 4 to 30 carbon atoms per molecule. For example, normal paraffin hydrocarbons containing about 10 to 18 carbon atoms per molecule are dehydrogenated by the subject method to produce the corresponding normal mono-olefin which can, in turn, be alkylated with benzene and sulfonated to make alkylbenzene sulfonate detergents having superior biodegradability. Likewise, n-alkanes having 10 to 18 carbon atoms per molecule can be dehydrogenated to the corresponding normal mono-olefin which, in turn, can be sulfonated or sulfated to make excellent detergents. Similarly, n-alkanes having 6 to 10 carbon atoms can be dehydrogenated to form the corresponding mono-olefin which can, in turn, be hydrated to produce valuable alcohols. Preferred feed streams for the manufacture of detergent intermediates contain a mixture of 4 or 5 adjacent normal paraffin homologues such as $C_{10}$ to $C_{13}$, $C_{11}$ to $C_{14}$, $C_{11}$ to $C_{15}$ and the like mixtures.

The sulfided multimetallic catalyst used in the present invention comprises a porous carrier material or support having combined therewith a uniform dispersion of catalytically effective amounts of a platinum or palladium component, an iridium component, a nickel component, a sulfur component, and, in the preferred case, an alkali or alkaline earth component.

Considering first the porous carrier material utilized in the present invention, it is preferred that the material be a porous, adsorptive, high-surface area support having a surface area of about 25 to about 500 m²/g. The porous carrier material should be relatively refractory to the conditions utilized in the dehydrogenation process, and it is intended to include within the scope of the present invention carrier materials which have traditionally been utilized in dual-function hydrocarbon conversion catalysts, such as: (1) activated carbon, coke, charcoal; (2) silica or silica gel, silicon carbide, clays, and silicates including those synthetically prepared and naturally occurring, which may or may not be acid treated, for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $MnAl_2O_4$, $CaAl_2O_4$, and other like compounds having the formula $MO.Al_2O_3$ where M is a metal having a valence of 2; and (7) combinations of elements from one or more of these groups. The preferred porous carrier material for use in the present invention are refractory inorganic oxides, with best results obtained with an alumina carrier material. Suitable alumina materials are the crystalline aluminas known as the gamma-, eta-, and theta-alumina, with gamma- or eta-alumina giving best results. In addition, in some embodiments the alumina carrier material may contain minor proportions of other well-known refractory inorganic oxides such as silica, zirconia, magnesia, etc.; however, the preferred support is substantially pure gamma- or eta-alumina. Preferred carrier materials have an apparent bulk density of about 0.2 to about 0.7 g/cc and surface area characteristics such that the average pore diameter is about 20 to about 300 Angstroms, the pore volume is about 0.1 to about 1 cc/g and the surface area is about 100 to about 500 m²/g. In general, best results are typically obtained with a gamma-alumina carrier material which is used in the form of spherical particles having: a relatively small diameter (i.e. typically about 1/16 inch), an apparent bulk density of about 0.2 to about 0.6 (most preferably about 0.3) g/cc, a pore volume of about 0.4 cc/g, and a surface area of about 150 to about 200 m²/g.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, etc., and utilized in any desired size. For the purpose of the present invention, a particularly preferred form of alumina is the sphere; and alumina spheres may be continuously manufactured by the well-known oil drop method which comprises: forming an alumina hydrosol by any of the techniques taught in the art and preferably by reacting aluminum metal with hydrochloric acid, combining the resulting hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° to about 400° F. and subjected to a calcination procedure at a temperature of about 850° to about 1300° F. for a period of about 1 to about 20 hours. It is a good practice to subject the calcined particles to a high temperature treatment with steam in order to remove undesired acidic components such as residual chloride. This procedure effects conversion of the alumina hydrogel to the corresponding crystalline gammaalumina. See the teachings of U.S. Pat. No. 2,620,314 for additional details.

One essential ingredient of the present catalytic composite is a nickel component. Best results are obtained when substantially all of this component is present in the composite in a sulfided state or in the elemental metallic state, or in a mixture of these states, and the preferred preparation procedure which is given in Example I is believed to result in this condition. The nickel component may be utilized in the composite in any amount which is catalytically effective, with the preferred amount being about 0.01 to about 5 wt. % thereof, calculated on an elemental nickel basis. Typically, best results are obtained with about 0.05 to about 2 wt. % nickel. It is, additionally, preferred to select the specific amount of nickel from within this broad weight range as a function of the amount of the platinum or palladium component, on an atomic basis, as is explained hereinafter.

The nickel component may be incorporated into the catalytic composite in any suitable manner known to those skilled in the catalyst formulation art. In addition, it may be added at any stage of the preparation of the composite — either during preparation of the carrier material or thereafter — since the precise method of incorporation used is not deemed to be critical. However, best results are obtained when the nickel component is relatively uniformly distributed throughout the carrier material, and the preferred procedures are the ones that are known to result in a composite having a relatively uniform distribution. One acceptable procedure for incorporating this component into the composite involves cogelling the nickel component during the preparation of the preferred carrier material, alumina. This procedure usually comprehends the addition of a soluble, decomposable compound of nickel such as nickel chloride to the alumina hydrosol before it is gelled. The resulting mixture is then finished by conventional gelling, aging, drying, and calcination steps as explained hereinbefore. One preferred way of incorporating this component is an impregnation step wherein the porous carrier material is impregnated with a suitable nickel-containing solution either before, during, or after the carrier material is calcined. Preferred impregnation solutions are aqueous solutions of water-soluble, decomposable nickel compounds such as nickel bromate, nickel bromide, nickel perchlorate, nickel chloride, nickel fluoride, nickel iodide, nickel nitrate, nickel sulfate, hexammine nickel (II) chloride, and the like compounds. Best results are ordinarily obtained when the impregnation solution is an aqueous solution of nickel chloride or nickel nitrate. This nickel component can be added to the carrier material, either prior to, simultaneously with, or after the other metallic components are combined therewith. Best results are usually achieved when this component is added simultaneously with the other metallic components. In fact, excellent results are obtained, as reported in the examples, with a one step impregnation procedure using an aqueous solution comprising chloroplatinic acid, nickel nitrate, nitric acid, and chloroiridic acid.

A second essential ingredient of the subject catalyst is the platinum or palladium component. That is, it is intended to cover the use of platinum or palladium or mixtures thereof as a second component of the present composite. It is an essential feature of the present invention that substantially all of this platinum or palladium component exists within the final catalytic composite in a sulfided state or in the elemental metallic state or in a mixture of these states. Generally, the amount of this component present in the final catalyst composite is small compared to the quantities of the other components combined therewith. In fact, the platinum or palladium component generally will comprise about 0.01 to about 2 wt. % of the final catalytic composite, calculated on an elemental basis. Excellent results are obtained when the catalyst contains about 0.05 to about 1 wt. % of platinum or palladium metal.

This platinum or palladium component may be incorporated in the catalytic composite in any suitable manner known to result in a relatively uniform distribution of this component in the carrier material such as coprecipitation or cogelation, ion exchange or impregnation. The preferred method of preparing the catalyst involves the utilization of a soluble, decomposable compound of platinum or palladium to impregnate the carrier material in a relatively uniform manner. For example, this component may be added to the support by commingling the latter with an aqueous solution of chloroplatinic or chloropalladic acid. Other water-soluble compounds of platinum or palladium may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, etc. The utilization of a platinum or palladium chloride compound, such as chloroplatinic or chloropalladic acid, is ordinarily preferred. Hydrogen chloride, nitric acid or the like acid is also generally added to the impregnation solution in order to further facilitate the uniform distribution of the metallic components throughout the carrier material. In addition, it is generally preferred to impregnate the carrier material after it has been calcined or oxidized in order to minimize the risk of washing away the valuable platinum or palladium compounds; however, in some cases it may be advantageous to impregnate the carrier material when it is in a gelled state.

Yet another essential ingredient of the present catalytic composite is an iridium component. It is of fundamental importance that substantially all of the iridium component exists within the catalytic composite of the present invention in the elemental state or in a sulfided state or in a mixture of these states and the subsequently described reduction and sulfiding procedure is designed to accomplish this objective. The iridium component may be utilized in the composite in any amount which is catalytically effective, with the preferred amount being about 0.01 to about 2 wt. % thereof, calculated on an elemental iridium basis. Typically best results are obtained with about 0.05 to about 1 wt. % iridium. It is, additionally, preferred to select the specific amount of iridium from within this broad weight range as a function of the amount of the platinum or palladium component, on an atomic basis, as is explained hereinafter.

This iridium component may be incorporated into the catalytic composite in any suitable manner known to those skilled in the catalyst formulation art which results in a relatively uniform dispersion of iridium in the carrier material. In addition, it may be added at any stage of the preparation of the composite — either during preparation of the carrier material or thereafter — and the precise method of incorporation used is not deemed to be critical. However, best results are thought to be obtained when the iridium component is relatively uniformly distributed throughout the carrier material, and the preferred procedures are the ones known to result in a composite having this relatively uniform distribution. One acceptable procedure for incorporating this component into the composite involves cogelling or coprecipitating the iridium component during the preparation of the preferred carrier material, alumina. This procedure usually comprehends the addition of a soluble, decomposable compound of iridium such as iridium tetrachloride to the alumina hydrosol before it is gelled. The resulting mixture is then finished by conventional gelling, aging, drying, and calcination steps as explained hereinbefore. A preferred way of incorporating this component is an impregnation step wherein the porous carrier material is impregnated with a suitable iridium-containing solution either before, during, or after the carrier material is calcined. Preferred impregnation solutions are aqueous solutions of water soluble, decomposable iridium compounds, such as iridium tribromide, iridium dichloride, iridium tetrachloride, iridium oxalic acid, iridium sulfate, potassium iridochloride, chloroiridic acid, sodium hexanitroiridate (III), and the like compounds. Best results are ordinarily obtained when the impregnation solution is an aqueous solution of chloroiridic acid or sodium chloroiridate. This component can be added to the carrier material, either prior to, simultaneously with, or after the other metallic components are combined therewith. Best results are usually achieved when this component is added simultaneously with the other metallic components. In fact, excellent results are obtained, as reported in the examples, with a one step impregnation procedure using an aqueous solution containing chloroplatinic acid, chloroiridic acid, nitric acid and nickel nitrate.

A highly preferred ingredient of the catalyst used in the present invention is the alkali or alkaline earth component. More specifically, this component is selected from the group consisting of the compounds of the alkali metals — cesium, rubidium, potassium, sodium, and lithium — and of the alkaline earth metals — calcium, strontium, barium, and magnesium. This component exists within the catalytic composite in an oxidation state above that of the elemental metal such as a relatively stable compound such as the oxide or sulfide, or in combination with one or more of the other components of the composite, or in combination with the carrier material such as, for example, in the form of an alkali or alkaline earth metal aluminate. Since, as is explained hereinafter, the composite containing the alkali or alkaline earth component is always calcined or oxidized in an air atmosphere before use in the conversion of hydrocarbons, the most likely state this component exists in during use in the dehydrogenation reaction is the corresponding metallic oxide such as lithium oxide, potassium oxide, sodium oxide, and the like. Regardless of what precise form in which it exists in the composite, the amount of this component utilized is preferably selected to provide a nonacidic composite containing about 0.1 to about 5 wt. % of the alkali metal or alkaline earth metal, and, more preferably, about 0.25 to 3.5 wt. %. Best results are obtained when this component is a compound of lithium or potassium. The function of this component is to neutralize any of the acidic material such as halogen which may have used in the preparation of the present catalyst so that the final catalyst is nonacidic.

This alkali or alkaline earth component may be combined with the porous carrier material in any manner known to those skilled in the art to result in a relatively uniform dispersion of this component throughout the carrier material with consequential neutralization of any acidic sites which may be present therein. Typically good results are obtained when it is combined by impregnation, coprecipitation, ion-exchange, and the like procedures. The preferred procedure, however, involves impregnation of the carrier material either before, during, of after it is calcined, or before, during, or after the other metallic ingredients are added to the carrier material. Best results are ordinarily obtained when this component is added to the carrier material after the other metallic components because the alkali metal or alkaline earth metal component acts to neutralize the acidic materials used in the preferred impregnation procedure for these metallic components. In fact, it is preferred to add the platinum or palladium, iridium and nickel components to the carrier material, oxidize the resulting composite in a wet air stream at a high temperature (i.e. typically about 600° to 1000° F.), then treat the resulting oxidized composite with steam or a mixture of air and steam at a relatively high temperature of about 800° to about 1050° F. in order to remove at least a portion of any residual acidity and thereafter add the alkali metal or alkaline earth component. Typically, the impregnation of the carrier material with this component is performed by contacting the carrier material with a solution of a suitable decomposable compound or salt of the desired alkali or alkaline earth metal. Hence, suitable compounds include the alkali metal or alkaline earth metal halides, sulfates, nitrates, acetates, carbonates, phosphates, and the like compounds. For example, excellent results are obtained by impregnating the carrier material after the other metallic components have been combined therewith, with an aqueous solution of lithium nitrate or potassium nitrate.

Regarding the preferred amounts of the various metallic components of the subject catalyst, I have found it to be a good practice to specify the amounts of the iridium component and the nickel component as a function of the amount of the platinum or palladium component. On this basis, the amount of the iridium component is ordinarily selected so that the atomic ratio of iridium to platinum or palladium metal contained in the composite is about 0.1:1 to about 2:1, with the preferred range being about 0.25:1 to about 1.5:1. Similarly, the amount of the nickel component is ordinarily selected to produce a composite coontaining an atomic ratio of nickel to platinum or palladium metal of about 0.2:1 to about 20:1, with the preferred range being about 1:1 to about 10:1. Similarly, the amount of the alkali or alkaline earth component is ordinarily selected to produce a composite having an atomic ratio of alkali metal or alkane earth metal to platinum or palladium metal of about 5:1 to about b 50:1 or more, with the preferred range being about 10:1 to about 25:1.

Another significant parameter for the instant sulfided nonacidic catalyst is the "total metals content" which is defined to be the sum of the platinum or palladium component, the iridium component, the nickel component, and the alkali or alkaline earth component, calculated on an elemental metal basis. Good results are ordinarily obtained with the subject catalyst when this parameter is fixed at a value of about 0.2 to about 5 wt. %, with best results ordinarily achieved at a metals loading of about 0.4 to about 4 wt. %.

Integrating the above discussion of each of the essential and preferred metallic components of the catalytic composite used in the present invention, it is evident that an especially preferred sulfided nonacidic catalytic composite comprises a combination of a platinum component, an iridium component, a nickel component, a sulfur component and an alkali or alkaline earth component with an alumina carrier material in amounts sufficient to result in the composite containing, on an elemental basis, from about 0.05 to about 1 wt. % platinum, about 0.05 to about 1 wt. % iridium, about 0.25 to about 3.5 wt. % of the alkali metal or alkaline earth metal, about 0.05 to about 2 wt. % nickel and about 0.05 to about 0.5 wt. % sulfur.

Regardless of the details of how the components of the catalyst are combined with the porous carrier material, the resulting multimetallic composite generally will be dried at a temperature of about 200° to about 600° F. for a period of from about 2 to about 24 hours or more, and finally calcined or oxidized at a temperature of about 600° to about 1100° F. in an air atmosphere for a period of about 0.5 to 10 hours, preferably about 1 to about 5 hours, in order to convert substantially all the metallic components to the corresponding oxide form. When acidic components are present in any of the reagents used to effect incorporation of any one of the components of the subject composite, it is a good practice to subject the resulting composite to a high temperature treatment with steam or with a mixture of steam and air, either before, during or after this oxidation step in order to remove as much as possible of the undesired acidic component. For example, when the platinum or palladium component is incorporated by impregnating the carrier material with chloroplatinic acid, it is preferred to subject the resulting composite to a treatment with steam or a mixture of steam and air, at a temperature of about 600 to 1100° F. in order to remove as much as possible of the undesired chloride.

It is an essential feature of the present invention that the resultant oxidized catalytic composite is subjected to a substantially water-free and hydrocarbon-free reduction step prior to its use in the conversion of hydrocarbons. This step is designed to selectively reduce substantially all of the platinum or palladium iridium and nickel components to the corresponding metals and to insure a uniform and finely divided dispersion of these metallic components throughout the carrier material. It is a good practice to dry the oxidized catalyst prior to this reduction step by passing a stream of dry air or nitrogen through same at a temperature of about 500° to 1100° F. at a GHSV of about 100 to 800 hr.$^{-1}$ until the effluent stream contains less than 1000 ppm $H_2O$ and preferably less than 500 ppm. Preferably substantially pure and dry hydrogen (i.e. less than 20 vol. ppm. $H_2O$) is used as the reducing agent in this step. The reducing agent is contacted with the oxidized catalyst at conditions including a temperature of about 800° to about 1200° F., a GHSV of about 300 to 1000 hr.$^{-1}$ and a period of time of about 0.5 to 10 hours effective to reduce substantially all of the platinum or palladium, iridium and nickel components to their elemental metallic state. This reduction treatment may be performed in situ as part of a start-up sequence if precautions are taken to predry the plant to a substantially water-free state and if substantially water-free and hydrocarbon-free hydrogen is used.

Another essential feature of the instant invention involves recognition that the resulting reduced catalytic composite can be beneficially subjected to a presulfiding operation with a sulfiding reagent designed to incorporate in the catalytic composite from about 0.01 to about 1 and more preferably about 0.05 to about 0.5 wt. % sulfur calculated on an elemental basis. I have found that it is critical to perform this presulfiding procedure to use of the catalytic composite in the conversion of hydrocarbons and after the metallic components are reduced to the corresponding elemental metallic states. The principal reason for this requirement is that it ensures that the uniform distribution of the metallic components in the carrier material will not be adversely affected by the sulfur. Preferably, this presulfiding treatment takes place in the presence of hydrogen and a suitable sulfur-containing decomposable sulfiding reagent such as hydrogen sulfide, lower molecular weight mercaptans, organic sulfides, etc. Typically, this procedure comprises treating the selectively reduced catalyst with a sulfiding gas such as a mixture of hydrogen and hydrogen sulfide having about 10 moles of hydrogen per mole of hydrogen sulfide at conditions sufficient to effect the incorporation of the desired amount of sulfur, generally including a temperature ranging from about 50° up to about 1100° F. or more. It is generally a good practice to perform this presulfiding step under substantially water-free conditions. The sulfided state of the instant catalyst can be maintained during the conversion process by continuously or periodically adding a sulfiding reagent to the reactor containing the catalyst in an amount corresponding to about 1 to 500 wt. ppm. of the hydrocarbon charge and preferably about 1 to 20 wt. ppm.

According to the method of the present invention, the dehydrogenatable hydrocarbon is contacted with the sulfided multimetallic catalytic composite described above in a dehydrogenation zone maintained at dehydrogenation conditions. This contacting may be accomplished by using the catalyst in a fixed bed system, a moving bed system, a fluidized bed systen, or in a batch type operation; however, in view of the danger of attrition losses of the valuable catalyst and of well-known operational advantages, it is preferred to use a fixed bed system. In this system, the hydrocarbon feed stream is preheated by any suitable heating means to the desired reaction temperture and then passed into a dehydrogenation zone containing a fixed bed of the catalyst previously characterized. It is, of course, understood that the dehydrogenation zone may be one or more separate reactors with suitable heating means therebetween to insure that the desired conversion temperature is maintained at the entrance to each reactor. It is also to be noted that the reactants may be contacted the catalyst bed in either upward, downward, or radial flow fashion with the latter being preferred. In addition, it is to be noted that the reactants, may be in the liquid phase, a mixed liquid-vapor phase, or a vapor phase when they contact the catalyst, with best results obtained in the vapor phase.

Although hydrogen is the preferred diluent for use in the subject dehydrogenation method, in some cases other art-recognized diluents may be advantageously utilized such as steam, methane, carbon dioxide, and the like diluents. Hydrogen is preferred because it serves the dual-function of not only lowering the partial pressure of the dehydrogenatable hydrocarbon, but also of suppressing the formation of hydrogen-deficient, carbonaceous deposits on the catalytic composite. Ordinarily, hydrogen is utilized in amounts sufficient to insure a hydrogen to hydrocarbon mole ratio of about 1:1 to about 20:1, with best results obtained in the range of about 1.5:1 to about 10:1. The hydrogen stream charged to the dehydrogenation zone will typically be recycled hydrogen obtained from the effluent stream from this zone after suitable hydrogen separation step. When utilizing hydrogen in the instant process, improved results are obtained if water of a water-producing substance (such as an alcohol, ketone, ether, aldehyde, or the like oxygen-containing decomposable organic compound) is added to the dehydrogenation zone in an amount calculated on the basis of equivalent water, corresponding to about 50 to about 10,000 wt. ppm. of the hydrocarbon charge stock, with about 1500 to 5000 wt. ppm. of water giving best results.

Regarding the conditions utilized in the process of the present invention, these are generally selected from the dehydrogenation conditions well known to those skilled in the art for the particular dehydrogenatable hydrocarbon which is charged to the process. More specifically, suitable conversion temperatures are selected from the range of about 700° to about 1200° F. With a value being selected from the lower portion of this range for the more easily dehydrogenated hydrocarbons such as the long chain normal paraffins and from the higher portion of this range for the more difficultly dehydrogenated hydrocarbons such as propane, butane, and the like hydrocarbons. For example, for the dehydrogenation of $C_6$ to $C_{30}$ normal paraffins, best results are ordinarily obtained at a temperature of about 800° to about 950° F. The pressure utilized is ordinarily selected at a value which is as low as possible consistent with the maintenance of catalyst stability and is usually about 0.1 to about 10 atmospheres with best results ordinarily obtained in the range of about 0.5 to about 3 atmospheres. In addition, a liquid hourly space velocity (calculated on the basis of the volume amount, as a liquid, of hydrocarbon charged to the dehydrogenation zone per hour divided by the volume of the catalyst bed utilized) is selected from the range of about 1 to about 40 hr.$^{-1}$, with best results for the dehydrogenation of long chain normal paraffins typically obtained at a relatively high space velocity of about 25 to 35 hr.$^{-1}$.

Regardless of the details concerning the operation of the dehydrogenation step, an effluent stream will be withdrawn therefrom. This effluent will usually contain unconverted dehydrogenatable hydrocarbons, hydrogen, and products of the dehydrogenation reaction. This stream is typically cooled and passed to a hydrogen-separation zone wherein a hydrogen-rich vapor phase is allowed to separate from a hydrocarbon-rich liquid phase. In general, it is usually desired to recover the unreacted dehydrogenatable hydrocarbon from this hydrocarbon-rich liquid phase in order to make the dehydrogenation process economically attractive. This recovery operation can be accomplished in any suitable manner known to the art such as by passing the hydrocarbon-rich liquid phase through a bed of suitable adsorbent material which has the capability to selectively retain the dehydrogenated hydrocarbons contained therein or by contacting same with a solvent having a high selectivity for the dehydrogenated hydrocarbon, or by a suitable fractionation scheme where feasible. In the case where the dehydrogenated hydrocarbon is a mono-olefin, suitable adsorbents having this capability are activated silica gel, activated carbon, activated alumina, various types of specially prepared zeolitic crystalline aluminosilicates, molecular sieves, and the like adsorbents. In another typical case, the dehydrogenated hydrocarbons can be separated from the unconverted dehydrogenatable hydrocarbons by utilizing the inherent capability of the dehydrogenated hydrocarbons to easily enter into several well-known chemical reactions such as alkylation, oligomerization, halogenation, sulfonation, hydration, oxidation, and the like reactions. Irrespective of how the dehydrogenated hydrocarbons are separated from the unreacted hydrocarbons, a stream containing the unreacted dehydrogenatable hydrocarbons will typically be recovered from this hydrocarbon separation step and recycled to the dehydrogenation step. Likewise, the hydrogen phase present in the hydrogen-separating zone will be withdrawn therefrom, a portion of it vented from the system in order to remove the net hydrogen make, and the remaining portion is typically recycled through suitable compressing means to the dehydrogenation step in order to provide diluent hydrogen therefor.

In a preferred embodiment of the present invention wherein long chain normal paraffin hydrocarbons are dehydrogenated to the corresponding normal mono-olefins, a preferred mode of operation of this hydrocarbon recovery step involves an alkylation reaction. In this mode, the hydrocarbon-rich liquid phase withdrawn from the hydrogen-separating zone is combined with a stream containing an alkylatable aromatic and the resulting mixture passed to an alkylation zone containing a suitable highly acid catalyst such as an anhydrous solution of hydrogen fluoride. In the alkylation zone the mono-olefins react with alkylatable aromatic while the unconverted normal paraffins remain substantially unchanged. The effluent stream from the alkylation zone can then be easily separated, typically by means of a suitable fractionation system, to allow recovery of the unreacted normal paraffins. The resulting stream of unconverted normal paraffins is then usually recycled to the dehydrogenation step of the present invention.

The following working examples are introduced to illustrate further the novelty, mode of operation, utility, and benefits associated with the dehydrogenation method and sulfided nonacidic multimetallic catalyst of the present invention. These examples of specific embodiments of the present invention are intended to be illustrative rather than restrictive.

These examples are all performed in a laboratory scale dehydrogenation plant comprising a reactor, a hydrogen separating zone, heating means, cooling means, pumping means, compressing means, and the like conventional equipment. In this plant, the feed stream containing the dehydrogenatable hydrocarbon is combined with a hydrogen stream containing water in an amount corresponding to about 2000 wt. ppm. of the hydrocarbon feed and the resultant mixture heated to the desired conversion temperature, which refers herein to the temperature maintained at the inlet to the reactor. The heated mixture is then passed into contact with the sulfided multimetallic catalyst which is maintained as a fixed bed of catalyst particles in the reactor. The pressures reported herein are recorded at the outlet from the reactor. An effluent stream is withdrawn from the reactor, cooled, and passed into the hydrogen-separating zone wherein a hydrogen gas phase separates from a hydrocarbon-rich liquid phase containing dehydrogenated hydrocarbons, unconverted dehydrogenatable hydrocarbons, and a minor amount of side products of the dehydrogenation reaction. A portion of the hydrogen-rich gas phase is recovered as excess recycle gas with the remaining portion being continuously recycled, after water addition as needed, through suitable compressing means to the heating zone as described above. The hydrocarbon-rich liquid phase from the separating zone is withdrawn therefrom and subjected to analysis to determine conversion and selectivity for the desired dehydrogenated hydrocarbon as will be indicated in the Examples. Conversion numbers of the dehydrogenatable hydrocarbon reported herein are all calculated on the basis of disappearance of the dehydrogenatable hydrocarbon and are expressed in mole percent. Similarly, selectivity numbers are reported on the basis of moles of desired hydrocarbon produced per 100 moles of dehydrogenatable hydrocarbon converted.

All of the catalysts utilized in these examples are prepared according to the following general method with suitable modification in stoichiometry to achieve the compositions reported in each example. First, an alumina carrier material comprising 1/16 inch spheres having an apparent bulk density of about 0.3 g/cc is prepared by: forming an alumina hydroxyl chloride sol by dissolving substantially pure aluminum pellets in a hydrochloric acid solution, adding hexamethylenetetramine to the resulting alumina sol, gelling the resulting solution by dropping it into an oil bath to form spherical particles of an alumina hydrogel, aging, and washing the resulting particles with an ammoniacal solution and finally drying, calcining, and steaming the aged and washed particles to form spherical particles of gamma-alumina containing substantially less than 0.1 wt. % combined chloride. Additional details as to this method of preparing this alumina carrier material are given in the teachings of U.S. Pat. No. 2,620,314.

The resulting gamma-alumina particles are then contacted at impregnation conditions with an aqueous impregnation solution containing chloroplatinic acid, nickel nitrate, chloroiridic acid, and nitric acid in amounts sufficient to yield a final multimetallic catalytic composite containing a uniform dispersion of the desired amounts of platinum, nickel and iridium. The nitric acid is utilized in an amount of about 5 wt. % of the alumina particles. In order to ensure a uniform dispersion of the metal moieties in the carrier material, the impregnation solution is maintained in contact with the carrier material particles for about ½ hour at a temperature of about 70° F. with constant agitation. The impregnated spheres are then dried at a temperature of about 225° F. for about an hour and thereafter calcined or oxidized in an air atmosphere containing about 5 to 25 vol. % $H_2O$ at a temperature of about 500° F to about 1000° F. for about 2 to 10 hours effective to convert all of the metallic components to the corresponding oxide forms. In general, it is a good practice to thereafter treat the resulting oxidized particles with an air stream containing about 10 to about 30% steam at a temperature of about 800° F to about 1000° F. for an additional period of about 1 to about 5 hours in order to reduce any residual combined chloride contained in the catalyst to a value of less than 0.5 wt. % and preferably less than 0.2 wt. %. In the cases shown in the examples where the catalyst utilized contains an alkali or alkaline earth component, this component is added to the oxidized and steam-treated multimetallic catalyst in a separate impregnation step. This second impregnation step involves contacting the oxidized multimetallic catalyst with an aqueous solution of a suitable decomposable salt of the alkali or alkaline earth component under conditions selected to result in a uniform dispersion of this component in the carrier material. For the catalyst utilized in the present examples, the salt is either lithium nitrate or potassium nitrate. The amount of the salt of the alkali metal utilized is chosen to result in a final catalyst having the desired nonacidic characteristics. The resulting alkali or alkaline earth impregnated particles are then preferably dried, oxidized, and steamed in an air atmosphere in much the same manner as is described above following the first impregnation step. In some cases, it is possible to combine both of these impregnation steps into a single step, thereby significantly reducing the time and complexity of the catalyst manufacturing procedure.

The resulting oxidized catalyst is thereafter subjected to a drying step which involves contacting the oxidized particles with a dry air stream at a temperature of about 1050° F., a GHSV of 300 hr.$^{-1}$ for a period of about 10 hours. The dried oxidized catalyst is then purged with a dry nitrogen stream and thereafter selectively reduced by contacting with a dry hydrogen stream at conditions including a temperature of about 870° F., atmospheric pressure and a gas hourly space velocity of about 500 hr.$^{-1}$ for a period of about 1 to 10 hours, effective to reduce substantially all of the platinum, nickel and iridium components to the corresponding elemental metals while maintaining the alkali or alkaline earth component in a positive oxidation state.

The resulting reduced catalyst particles are then contacted with a sulfiding gas comprising a mixture of a mixture of $H_2S$ and $H_2$ in a mole ratio of 1:10 at a temperature of about 1050° F., atmospheric pressure and a GHSV of about 800 hr.$^{-1}$ for a period of about ½ hour effective to produce a sulfided catalyst containing, on an elemental basis, about 0.2 wt. % sulfur.

EXAMPLE I

The reactor is loaded with 100 cc of a sulfided catalyst containing, on an elemental basis, 0.375 wt. % platinum, 0.375 wt. % iridium, 0.5 wt. % nickel, 0.2 wt. % sulfur, and less than 0.15 wt. % chloride. The feed stream utilized is commercial grade isobutane containing 99.7 wt. % isobutane and 0.3 wt. % normal butane.

The feed stream is contacted with the catalyst at a temperature of 1065° F., a pressure of 10 psig., a liquid hourly space velocity of 4.0 hr.$^{-1}$, and a hydrogen to hydrocarbon mole ratio of 2:1. The dehydrogenation plant is lined-out at these conditions and a 20 hour test period commenced. The hydrocarbon product stream from the plant is continuously analyzed by GLC (gas liquid chromatography) and a high conversion of isobutane is observed with a high selectivity for isobutylene.

EXAMPLE II

The sulfided nonacidic catalyst contains, on an elemental basis, 0.375 wt. % platinum, 0.2 wt. % iridium, 0.5 wt. % nickel, 0.2 wt. % sulfur, 0.6 wt. % lithium, and 0.15 wt. % combined chloride. The feed stream is commercial grade normal dodecane. The dehydrogenation reactor is operated at a temperature of 870° F., a pressure of 10 psig., a liquid hourly space velocity of 32 hr.$^{-1}$, and a hydrogen to hydrocarbon mole ratio of 8:1. After a line-out period, a 20 hour test period is performed during which the average conversion of the normal dodecane is maintained at a high level with a selectivity for normal dodecene of about 90%.

EXAMPLE III

The sulfided nonacidic catalyst is the same as utilized in Example II. The feed stream is normal tetradecane. The conditions utilized are a temperature of 840°F., a pressure of 20 psig., a liquid hourly space velocity of 32 hr.$^{-1}$, and a hydrogen to hydrocarbon mole ratio of 8:1. After a line-out period, a 20 hour test shows an average conversion of about 12%, and a selectivity for normal tetradecene of about 90%.

EXAMPLE IV

The sulfided nonacidic catalyst contains, on an elemental basis, 0.25 wt. % platinum, 0.25 wt. % iridium, 0.25 wt. % nickel, 0.2 wt. % sulfur, and 0.6 wt. % lithium, with combined chloride being less than 0.2 wt. %. The feed stream is substantially pure cyclohexane. The conditions utilized are a temperature of 950°F., a pressure of 100 psig., a liquid hourly space velocity of 3.0 hr.$^{-1}$, and a hydrogen to hydrocarbon mole ratio of 5:1. After a line-out period, a 20 hour test is performed with almost quantitative conversion of cyclohexane to benzene and hydrogen.

EXAMPLE V

The sulfided nonacidic catalyst contains, on an elemental basis, 0.2 wt. % platinum, 0.2 wt. % iridium, 0.5 wt. % nickel, 0.2 wt. % sulfur, 1.5 wt. % potassium, and less than 0.2 wt. % combined chloride. The feed stream is commerical grade ethylbenzene. The conditions utilized are a pressure of 15 psig., a liquid hourly space velocity of 32 hr. $^{-1}$, a temperature of 1050° F., and a hydrogen to hydrocarbon mole ratio of 8:1. During a 20 hour test period, 85% or more of equilibrium conversion of the ethylbenzene is observed. The selectivity for styrene is about 95%.

It is intended to cover by the following claims, all changes and modifications of the above disclosure of the present invention which would be self-evident to a man of ordinary skill in the catalyst-formulation art or in the hydrocarbon dehydrogenation art.

I claim as my invention:

1. A sulfided catalytic composite comprising a porous carrier material containing, on an elemental basis, about 0.01 to about 2 wt. % platinum or palladium, about 0.01 to about 2 wt. % iridium, about 0.01 to about 5 wt. % nickel and about 0.01 to about 1 wt. % sulfur; wherein the platinum or palladium, iridium, and nickel are uniformly dispersed throughout the porous carrier material; wherein substantially all of the platinum or palladium, iridium and nickel are present therein in the elemental metallic state or in a sulfided state; and wherein the composite is sulfided, prior to contact with the dehydrogenatable hydrocarbon and after substantially all of the platinum or palladium, iridium and nickel contained therein have been reduced to the corresponding elemental metallic state, by treatment with a sulfiding gas at conditions selected to incorporate about 0.01 to about 1 wt. % sulfur.

2. A catalytic composite as defined in claim 1 wherein the porous carrier material is a refractory inorganic oxide.

3. A catalytic composite as defined in claim 2 wherein the refractory inorganic oxide is alumina.

4. A catalytic composite as defined in claim 1 wherein the composite contains, on an elemental basis, about 0.05 to about 1 wt. % platinum or palladium, about 0.05 to about 1 wt. % iridium, about 0.05 to about 2 wt. % nickel and about 0.05 to about 0.5 wt. % sulfur.

5. A catalytic composite as defined in claim 1 wherein the atomic ratio of nickel to platinum or palladium in the composite is about 0.2:1 to about 20:1.

6. A catalytic composite as defined in claim 1 wherein the matals content of the catalytic composite is adjusted so that the atomic ratio of iridium to platinum or palladium is about 0.1:1 to about 2:1.

7. A sulfided nonacidic catalytic composite comprising a porous carrier material containing, on an elemental basis, about 0.01 to about 2 wt. % platinum or palladium, about 0.01 to about 2 wt. % iridium, about 0.1 to about 5 wt. % alkali metal or alkaline earth metal, about 0.01 to about 5 wt. % nickel, and about 0.01 to about 1 wt. % sulfur; wherein the platinum or palladium, iridium, alkali metal or alkaline earth metal and nickel are uniformly dispersed throughout the porous carrier material; wherein substantially all of the platinum or palladium, nicke and iridium are present in the elemental metallic state or in a sulfided state; wherein substantially all of the alkali metal or alkaline earth metal is present in an oxidation state above that of the elemental metal; and wherein the composite is sulfided, prior to contact with any hydrocarbon and after substantially all of the platinum or palladium, iridium and nickel contained therein have been reduced to the corresponding elemental metallic state, by treatment with a sulfiding gas at conditions selected to incorporate about 0.01 to about 1 wt. % sulfur.

8. A catalytic composite as defined in claim 7 wherein the porous carrier materials is a refractory inorganic oxide.

9. A catalytic composite as defined in claim 8 wherein the refractory inorganic oxide is alumina.

10. A catalytic composite as defined in claim 7 wherein the alkali metal or alkaline earth metal is potassium.

11. A catalytic composite as defined in claim 7 wherein the alkali metal or alkaline earth metal is lithium.

12. A catalytic composite as defined in claim 7 wherein the sulfiding gas is a mixture of hydrogen and hydrogen sulfide.

13. A catalytic composite as defined in claim 7 wherein the composite contains, on an elemental basis, about 0.05 to about 1 wt. % platinum or palladium, about 0.05 to about 1 wt. % iridium, about 0.25 to about 3.5 wt. % alkali metal or alkaline earth metal, about 0.05 to about 2 wt. % nickel and about 0.05 to about 0.5 wt. % sulfur.

14. A catalytic composite as defined in claim 7 wherein the metals contents thereof is adjusted so that the atomic ratio of iridium to platinum or palladium is about 0.1:1 to about 2:1, the atomic ratio of alkali metal or alkaline earth metal to platinum or palladium is about 5:1 to about 50:1 and the atomic ratio of nickel to platinum or palladium is about 0.2:1 to about 20:1.

* * * * *